United States Patent [19]

Heusser

[11] Patent Number: 5,025,660

[45] Date of Patent: Jun. 25, 1991

[54] APPARATUS AND METHOD FOR THE AUTOMATIC DETERMINATION OF THE COUNT OF A TEXTILE TEST SAMPLE

[75] Inventor: Eduard Heusser, Uster, Switzerland

[73] Assignee: Zellweger Uster AG, Uster, Switzerland

[21] Appl. No.: 364,431

[22] PCT Filed: Sep. 28, 1988

[86] PCT No.: PCT/CH88/00175

§ 371 Date: May 19, 1989

§ 102(e) Date: May 19, 1989

[87] PCT Pub. No.: WO89/03531

PCT Pub. Date: Apr. 20, 1989

[30] Foreign Application Priority Data

Oct. 6, 1987 [CH] Switzerland ............... 03907/87

[51] Int. Cl.⁵ .................. G01N 33/36; G01N 5/00
[52] U.S. Cl. ........................... 73/160; 364/568
[58] Field of Search ............ 73/160, 159; 364/561, 364/562, 567, 568

[56] References Cited

U.S. PATENT DOCUMENTS

| | | | |
|---|---|---|---|
| 2,844,028 | 7/1958 | Benn | 73/160 |
| 3,181,354 | 5/1965 | Cashore | 73/159 |
| 3,751,981 | 8/1973 | Jernigan et al. | 73/160 |
| 3,754,172 | 8/1973 | Hoffmann | 361/280 |
| 3,788,138 | 1/1974 | Heusser | 73/160 |
| 3,828,869 | 8/1974 | Sellers | 364/568 |
| 3,857,023 | 12/1974 | McCall | 364/568 |
| 4,083,002 | 4/1978 | Allport | 364/568 |
| 4,084,434 | 4/1978 | Goodrich et al. | 73/160 |
| 4,116,393 | 9/1978 | Inouye et al. | 73/160 |
| 4,733,829 | 3/1988 | Mima | 73/160 |
| 4,843,879 | 7/1989 | Enderlin et al. | 73/160 |
| 4,845,983 | 7/1989 | Heusser | 73/160 |

FOREIGN PATENT DOCUMENTS

| | | | |
|---|---|---|---|
| 129076 | 12/1984 | European Pat. Off. | |
| 1940291 | 2/1971 | Fed. Rep. of Germany | |
| 2152935 | 10/1971 | Fed. Rep. of Germany | |
| 3402181 | 7/1985 | Fed. Rep. of Germany | 73/160 |
| 243242 | 9/1969 | U.S.S.R. | 73/159 |
| 2192722 | 1/1988 | United Kingdom | |

*Primary Examiner*—William A. Cuchlinski, Jr.
*Assistant Examiner*—Diego F. F. Gutierrez
*Attorney, Agent, or Firm*—Burns, Doane, Swecker & Mathis

[57] ABSTRACT

Apparatus for automatically determining the count of textile yarns containing a device for taking off definite lengths of a test sample from a supply, scales (19), and an evaluation unit. Means (20) are provided in the path of the test sample upstream of the scales for forming the length of yarn in each test sample into a ball-like bundle (K) for weighing. The ball-like bundle ensures that parts of the test sample do not hang over the edge of the scale pan (23) or become entangled somewhat so as to distort the determination of the weight. The ball-like bundle may be blown from the scale pan simply and safely after a weighing operation by an air jet. The high processing capacity the apparatus permits it to be interfaced with other test apparatus without any problem.

18 Claims, 5 Drawing Sheets

APPARATUS AND METHOD FOR THE AUTOMATIC DETERMINATION OF THE COUNT OF A TEXTILE TEST SAMPLE

The invention relates to apparatus and methods for the automatic determination of the count of a textile test sample in the form of yarns, rovings or slivers.

In textile practice, such determinations of count are important. For example fluctuations in fineness (also referred to as fluctuations in count), which are fluctuations in the weight per unit length of a yarn may lead to weft bars in woven fabrics and to irregularities in knitted goods. In order to avoid these losses in quality as far as possible, determinations of count (or count checks) are carried out continuously in the textile laboratories of spinning mills. Such count checks make it possible to detect and eliminate machine setting and operating errors as quickly as possible.

In the past, these count checks have been done semi-automatically in the laboratory. Lengths of the test sample are taken off from a bobbin more or less manually and laid, likewise manually, on the scales. The evaluation then takes place automatically. Bearing in mind that other test apparatuses used in textile laboratories (such as, for example, the tester sold by Zellweger Uster AG under the trademark USTER TESTER, process a few hundred meters of yarn per minute, it becomes clear that determinations of count can be made only by sampling. Because of the comparatively modest yarn processing capacity of the conventional count check apparatus, it has not been feasible to interface, such test apparatus with other test apparatuses, such as, for example, evenness testers. However, such interfacing would be an important step in the direction of an automatic textile laboratory.

Some proposals have recently been made for automating the determination of count. Two of these are described in DE-A-3,402,181 and EP-A-129,076. In each case, there is a proposal for the combination with an evenness tester of an apparatus for the determination of count having scales downstream of the evenness tester. Essentially, the evenness tester contains a measuring element and a take-off means formed by a pair of rollers, and the scales are arranged immediately below the take-off means.

In this way, the length of the test sample required for a determination of count, usually at least 100 meters, is transported into the scale pan by the take-off rollers and gravity. However, has been found that the measurement results are intolerably distorted even by the tiniest length of test sample hanging over the edge of the scale pan or becoming entangled somewhere. Since such distortion occur relatively often, the measurement results are not reproducable and not reliable, so that these known apparatuses have not yet become fully acceptable.

There are, moreover, two further disadvantageous properties: on the one hand, the continuous transport of the test sample into the scale pan has a negative effect on the tarings and zero constancy of the scales, and, on the other hand, the removal of the test sample lying in the scale pan after measurement is equally disadvantageous because it requires undesirably strong shocks of compressed air. Again, these apparatuses are limited as regards the rate of transport.

The present invention provides features useful in methods and apparatus for making automatic count checks and for yielding more exact and reliable measurement results. Another aspect of the invention permits the test sample to be removed from the scale pan smoothly and without difficulty.

According to the invention, means are arranged in the path of the test sample upstream of the scales for forming the test sample taken off at any one time into a ball-like bundle.

Whereas earlier proposals provided for the test sample to be transported into the scale pan without any additional manipulation, the present invention envisions forming a test sample into a ball-like bundle before deposition onto the scale pan. This guarantees that parts of the test sample do not hang over the edge of the scale pan or become entangled somewhere and, in addition, after measurement it is possible to remove the ball simply, whether by blowing or with a mechanical element.

The invention further relates to a combination of the count check apparatus with an evenness testing device. In this combination the count check apparatus is connected to the evenness tester via a transport line and to its evaluation unit.

According to the invention, then, the evenness tester and apparatus for the determination of count are no longer united in a common housing. However, it is precisely this which decisively improves the further automation of the textile laboratory.

The invention is explained below with the aid of an illustrative embodiment and the drawings, in which.

Figure 1:
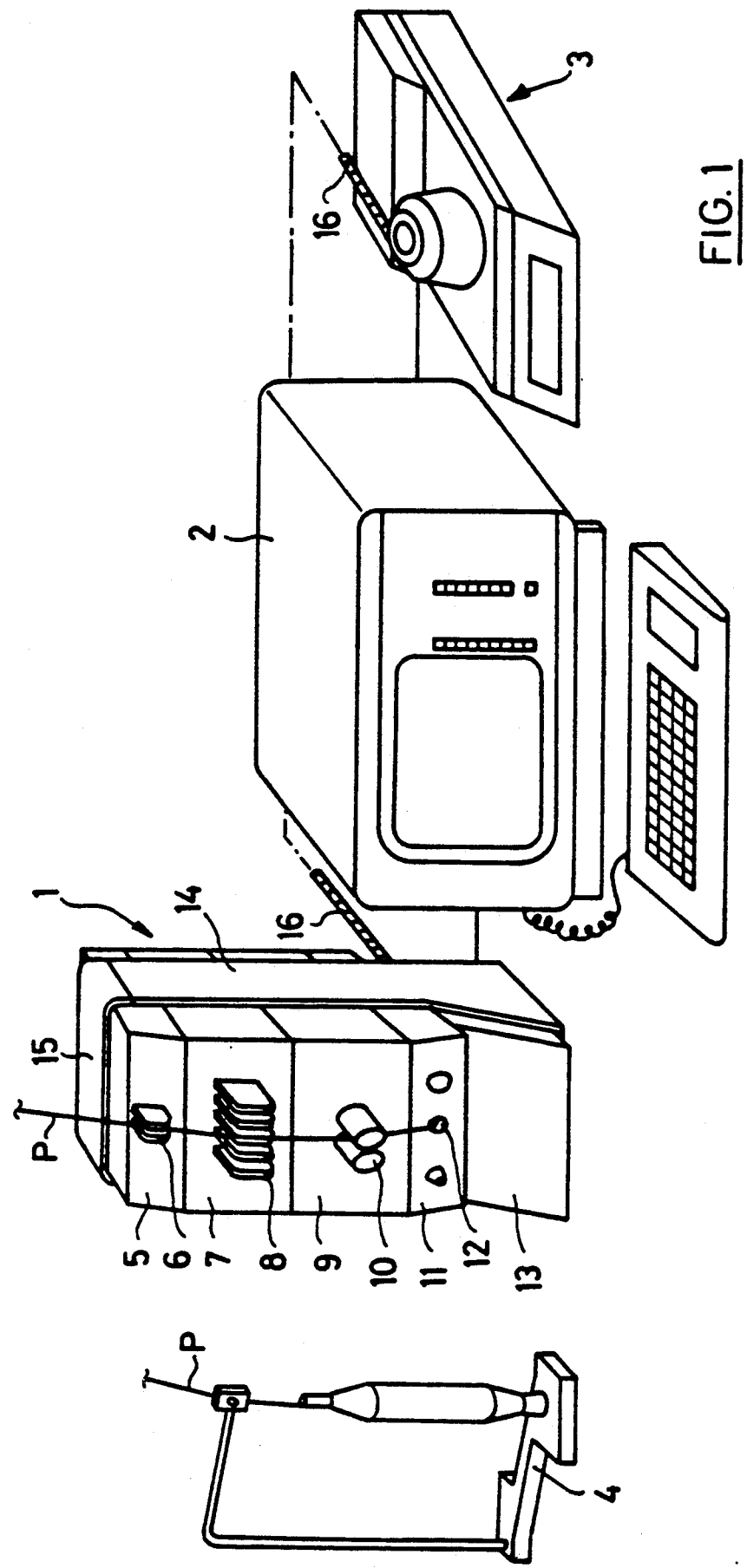
FIG. 1 shows a perspective representation of a yarn test apparatus having an evenness tester and a device for determination of count.

The yarn test apparatus represented in FIG. 1 consists of an evenness tester 1 for determining the weight fluctuations of textile test sample, such as yarns, rovings or slivers of staple fibres, an operating/evaluation unit 2, a count tester 3, and a stand 4 for the handling units with the test samples P, which are, for example, yarn or roving bobbins. With the exception of the count tester 3, yarn test apparatuses of this type are known and are, for example marketed worldwide by Zellweger Uster AG under the trademark USTER TESTER.

Instead of the evenness tester 1 as shown (that is, a tester for samples made of staple fibres), it also is possible to use an evenness tester for continuous filament yarns which, although deviating slightly in construction from the evenness tester as shown, corresponds with it in principle. In this connection reference is made to GB-A-2 192 722, the disclosure of which is incorporated herein by reference. It is also shown in this patent application that the yarn test apparatus normally also has an output unit in the form of a printer; for reasons of space, this printer is left out of FIG. 1, but will be present in most cases.

According to the representation, the evenness tester 1 for the test sample P consists of several modules which are arranged as follows in the transport direction of the test sample P, that is from top to bottom in the figure: Initially a module 5 with a thread guidance device 6, for example a thread break, followed by a module 7 with a measuring element 8, followed by a module 9 with a feed device 10, and followed by a module 11 with a suction exhaust nozzle 12. The lowermost module 11 is mounted on a base 13, and all the named modules 5,7,9 and 11, in conjunction with the base 13, are arranged in a frame 14 with an arch-like upper part 15, and held by this frame.

The measuring element 8, through which the test sample P drawn by the feed device 10 in the form of a pair of rollers, is a so-called capacitive measuring element. This is described in the U.S. Pat. Nos. 3,754,172 and 3,788,138, the disclosure of which is incorporated herein by reference. The feed device 10, which is formed by a pair of transport rollers, is known from the already mentioned USTER TESTER, and will not be futher described here. Detailed descriptions of parts of the eveness tester 1 are to found in the European patent applications EP-A-266 611, EP-A-266 612, EP-A-266 614 and EP-A-266 615.

Among other things, the operating/evaluation unit 2 contains an A-D converter and a computer, and according to the representation is combined with a screen. The electrical signals continually generated by the measuring element 8 are processed via the computer of the evaluation unit 2, and stored in a suitable form in a memory integrated in the evaluation unit 2, and can be displayed on the screen before being printed out on the printer (not shown). This has the advantage that all the data arriving can first be displayed on the screen, designating only selected data for printout on the printer.

The signals generated by the measuring element 8 are representative of the test sample cross-section, and are processed in the operating/evaluation unit to produce the following characteristics, for example: spectrogram (wavelength spectrum of the weight fluctuations); classification and enumeration of extreme positions with the imperfection indicator; variation coefficient and length variation curve. All these characteristics are known from the USTER TESTER already mentioned.

A hose-pipe or line 16 is connected to the suction exhaust nozzle 12 and leads to the count tester 3, so that it transports the test sample P by the action of compressed air in order to have its count determined once the evenness testing has been done. Since the fineness or count of a yarn is given as weight per unit length (e.g. in grammes per meter), the determination of count is a determination of the weight of a definite length of a test sample. The evenness tester 1 processes and tests up to a few hundred meters of test sample per minute, the length of test sample P taken off and transported per unit time by the transport rollers 10 being given by the rotational speed of the transport rollers 10. On the other hand, if this rotational speed is known, then the length of test sample transported is determined by the time during which the test sample is transported.

Consequently, in operating the evenness tester 1, in which the rate of transport of the said test sample P is set and therefore known, all that is required is to use a counter or timer to control a cutting element in such a way that the test sample is cut off on each occasion after a certain length of, for example, 100 meters (see FIGS. 6 and 7a to 7d).

The cut-off pieces of the test sample P are blown through the hose-pipe 16 to the count tester 3 where they are weighed, and the count is computed in the operating/evaluation unit, it being possible to compute and indicate various results, such as individual values, average values, group values from measurement series, variation coefficients, etc.

In the module 11 a switch point with cutting elements (see FIGS. 6 and 7a to 7d) is provided through which the pieces of test sample can, as desired, be directed either to the count tester 3 or to a waste container.

Figure 3:
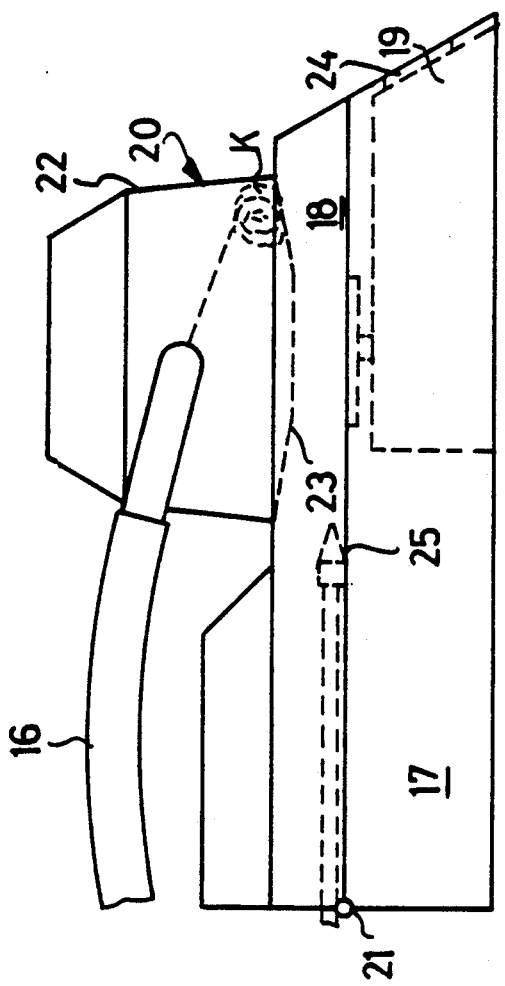
FIGS. 2 and 3 show a schematic representation of the device for determination of count in two views.
Figure 2:
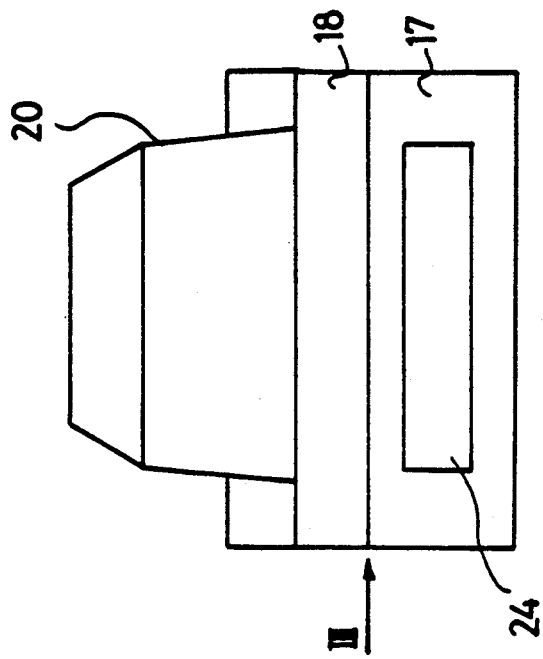
Figure 4:
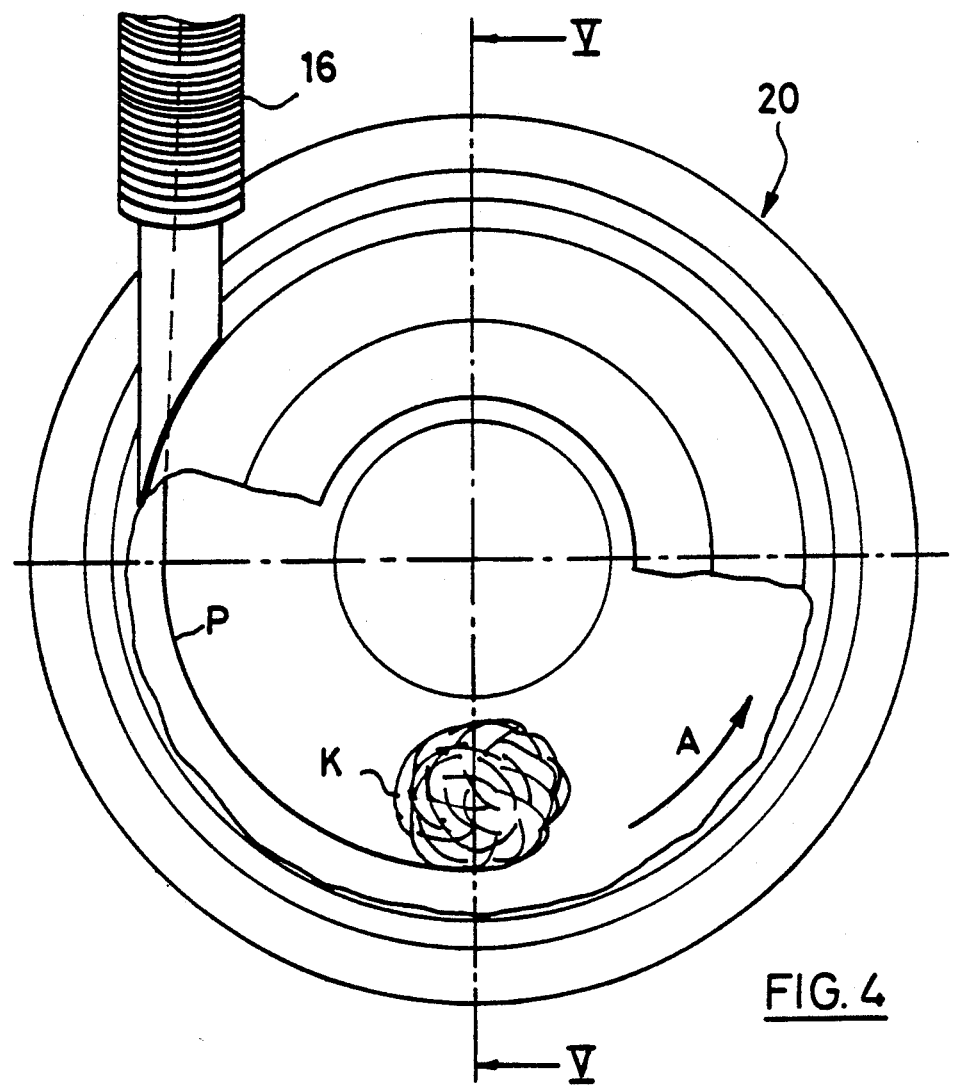
FIGS. 4 and 5 show a detail of the device for determination of count in two views.
Figure 5:
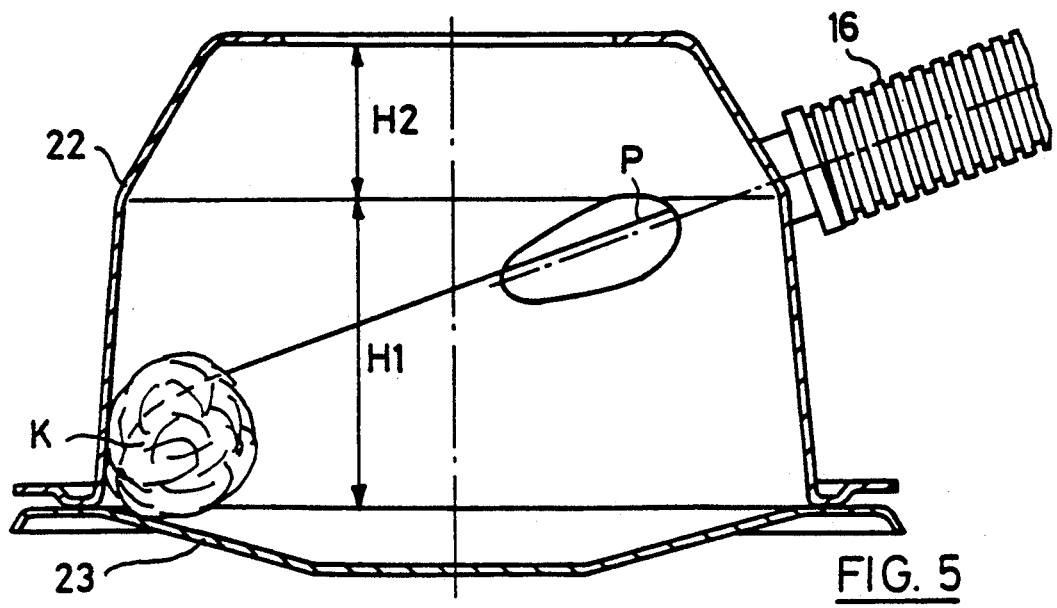

The count tester 3 is represented in detail in FIGS. 2 to 5, in which FIG. 2 shows a front view and FIG. 3 a side view in the direction of the arrow III of FIG. 2; FIG. 4 shows a partially cut-away plan view of a detail of FIG. 2 and FIG. 5 shows a section along the line V—V of FIG. 4.

According to the representation, the count tester 3 consists of a two-part housing with a lower and an upper housing part 17 and 18 respectively, with electronic scales 19 built into the lower housing part 17, and with a bell-shaped container 20, mounted on the upper housing part 18, in which the line 16 (FIG. 1) ends. The container 20 is represented in detail in FIGS. 4 and 5.

The two housing parts 17 and 18 are connected with each other via a swivel axis 21, about which the upper part 18 can be pivoted relative to the lower part. An appropriate motor and drive are disposed in the left-hand half of the housing 17, 18 in FIG. 3 (and therefore in the rear half in FIG. 2).

The container 20 consists of a bell-shaped cover 22 open at the top, and a plate-shaped base 23, which can be moved up and down relative to the cover 22. A special drive mechanism (not represented) is likewise provided in the housing 17, 18 for this up and down movement during which the base 23 is lowered onto the scales 19.

The mode of operation of the count tester 3 is as follows: As soon as the count of a test sample is to be determined, the latter is blown through the line 16 at the predetermined length into the container 20, where it is formed into a ball K by virtue of the effect of the blown air and of the shape and the dimensioning of the container 20. After the predetermined length of test sample has been transported into the container 20, it lies on the base 23 in the form of the ball K. The base 23 with the ball K is now lowered onto the tared scales 19. The scales 19 measure the weight of the base 23 and ball, subtract the known weight of the base 23, and exhibit the net weight of the ball in a display field 24. Naturally, the weight is also delivered to the operating/evaluation unit 2 for determination of the count and, possibly, of other parameters derived therefrom.

As soon as the determination of the weight of the ball is finished, which is the case, for example, when there is no longer any change in the weight measured by the scales 19, the upper housing part 18, together with the cover 22, is swivelled upwards about the axis 21, far enough to form between cover 22 and base 23 a gap enabling the further transportation of the ball K. A blow nozzle 25 firmly fixed in the lower housing part 17 is then actuated with compressed air, so that the ball K is blown out of the base 23 and into a waste container (not represented).

Essential to the mode of operation as described is the formation of the ball K, which is achieved by the interaction of the blown air in the line 16 and the container 20. It would, of course, be possible for the transport of the test sample in the line 16 to be done with mechanical means instead of with air. The other functional steps described, such as the lowering of the base 23 onto the scales 19, the swivelling up of the housing 17, 18 and the blowing out of the ball K from the base 23 are to be understood as merely exemplary and not exclusive.

As may be seen from FIGS. 4 and 5, the cover 22 of the housing 20 has a bell-shaped form and consists of two frustum-shaped parts with different angles of slope. The wall of the lower part, with a height of H1, has a slope of 70° to 90°, preferably approximately 85°, the wall of the upper part, with a height of H2, has a slope of 45° to 75°, preferably approximately 60°.

The height H1 is approximately twice as large as H2. At the upper end, the cover 22 is provided with an opening, the lower, open end is closed by the base 23 during the formation of a ball K.

The line 16 ends in the cover 22, doing so in a tangential plane at an acute angle of less than 45°, preferably of approximately 20° to the horizontal, the exit lying slightly below the zone of transition between the lower and upper parts of the cover 22. Test sample P is blown by the air in the line 16 against the inner wall of the lower part of the cover, and thereby glides along this wall in the direction of the arrow A (FIG. 4), moving spirally downwards. As soon as the test sample P thereby lands on the base 23, a ball K is formed.

Because of this ball K, the determination of the weight of a measured length, and thus of the count of the test sample, is rendered reliable and reproducable. This result is surprising to the expert and not predictable. Moreover, after the determination of weight the ball can easily be removed from the housing 20 (FIG. 3, blow nozzle 25). In this way, the count tester 3 as described enables a fully automatic determination of count at high rates of testing as well which provides an essential step in the direction of automatic textile laboratories.

Although the illustrative embodiment as described provides a description of the count tester according to the invention in conjunction with an evenness tester, its application is in no way restricted to this combination, and can be varied within wide limits. All that is essential is the presence of a take-off and supply means for definite lengths of test sample, and an evaluation unit connected to the scales. Clearly, then, it is even conceivable to develop the count tester into a self-contained test apparatus with its own supply means for the test sample and a built-in evaluation module.

Figure 6:
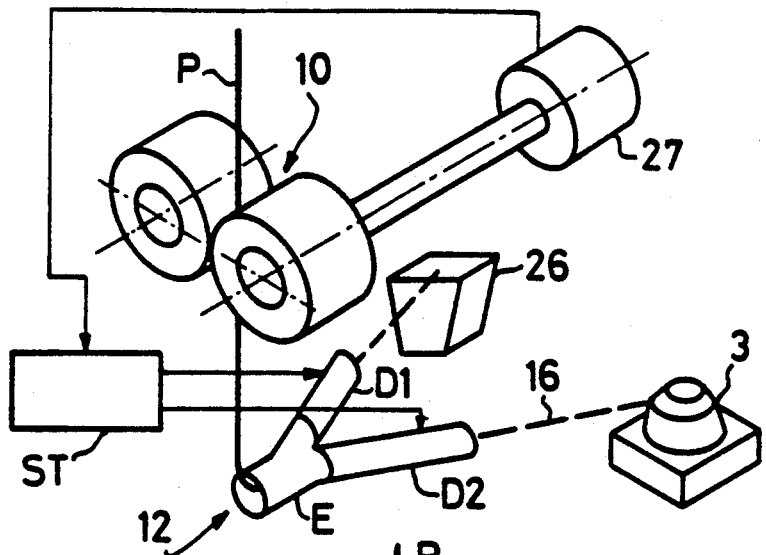
FIG. 6 shows a schematic representation of a detail of the evenness tester of FIG. 1.
Figure 7A:
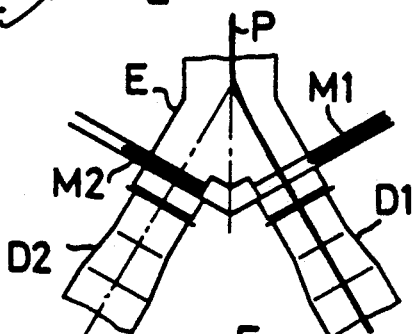
FIGS. 7 and 8 show function-illustrating diagrams.
Figure 7B:
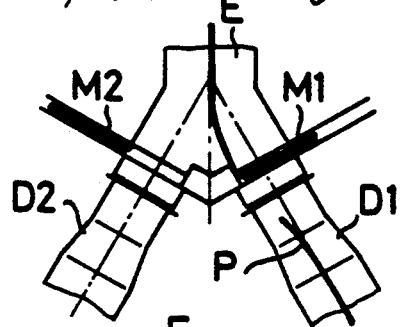
Figure 7C:
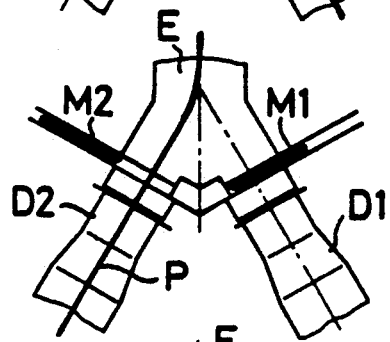
Figure 7D:
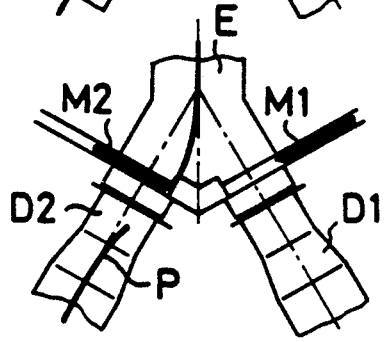

FIG. 6 shows schematicly the pair of rollers of the feed device 10 and the suction exhaust nozzle 12 (FIG. 1) which is designed as a switch point for the alternative transport of the test sample P to the count tester 3 or to a waste container 26. FIGS. 7a to 7d show the suction exhaust nozzle 12 in different operating conditions and FIG. 8 shows function-illustrating diagrams.

According to the representation, the suction exhaust nozzle 12 consists of two nozzles D1 and D2 which are connected to a common intake E. The nozzles D1 and D2 branch forkedly off the intake E and are individually actuable with compressed air. The said nozzles are preferable so-called Coanda nozzles as described in FR-A-2 606 883. Between each nozzle D1, D2 and the intake E is provided a controllable cutting element M1, M2 respectively. A line which leads to a waste container 26 is connected to the nozzle D1 and the hosepipe 16 leading to the count tester 3 is connected to the nozzle D2. The nozzles D1, D2 and the cutting elements M1, M2 are controlled by a control unit ST by means of a tachometer signal which is picked up from a transmitting-type device 27 the latter being connected with one of the rollers 10. The tachometer signal is shown in FIG. 8, line b. It consists of square-wave impulses the number of which being proportional to the length of the test sample P drawn off by the pair of rollers 10. Accordingly into the x-axis of FIG. 8 there are entered both the time t and the drawn-off length L of the test sample.

Figure 8:
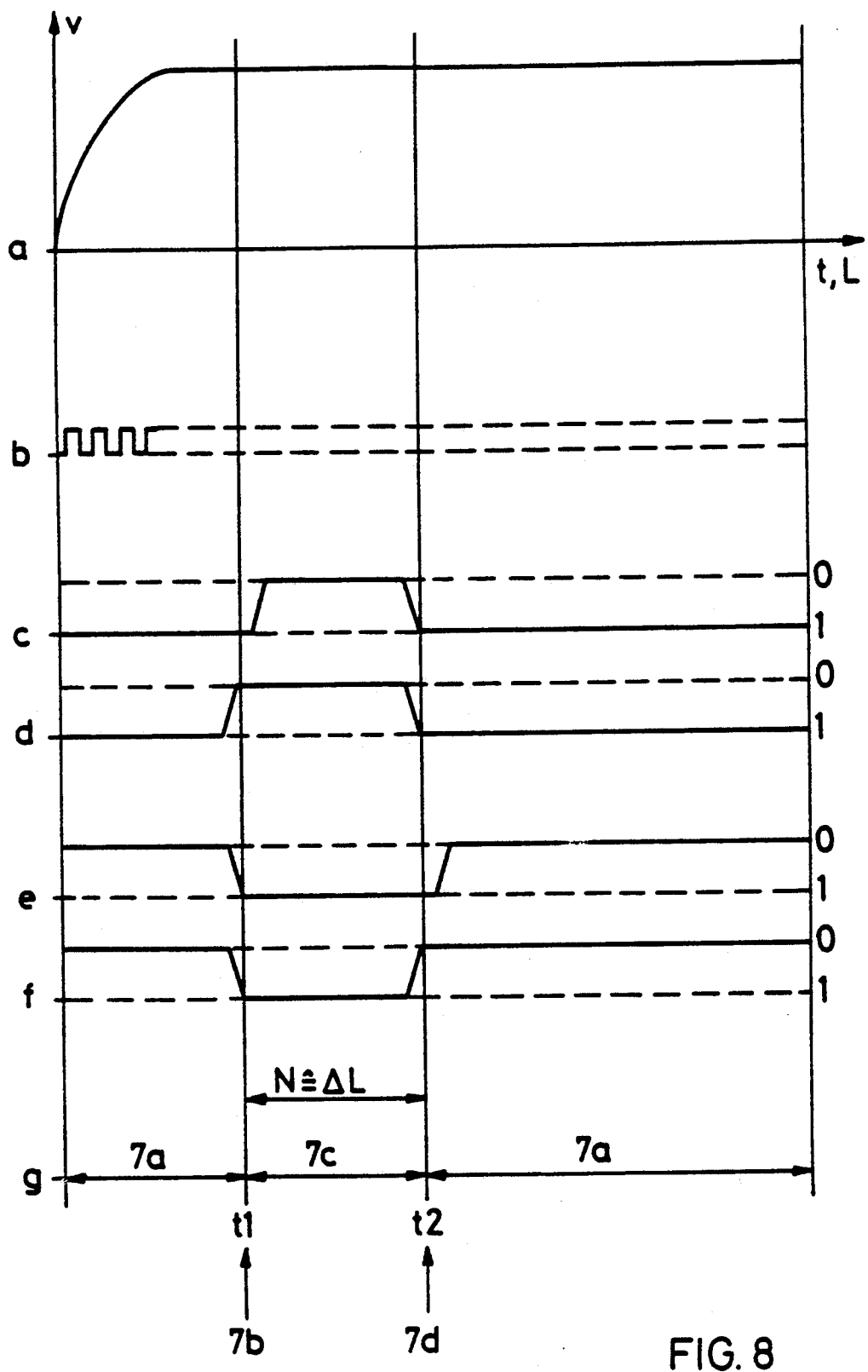

Moreover, FIG. 8 shows in line a the velocity v of the test sample P, in lines c and d the selection of the nozzle D1 and of the cutting element M1 respectively, in lines e and f the selection of the nozzle D2 and of the cutting element M2 respectively, and in line g the operating conditions in accordance with the diagrams of FIG. 7. In lines c and e the symbols "0" and "1" characterize the conditions "nozzle not in operation" and "nozzle in operation" respectively, and in lines d and f the symbols "1" and "0" characterize the conditions "cutting element open" and "cutting element closed" respectively.

At the start of a measurement a certain time passes until the velocity v of the test sample P has reached the predetermined value. Therefore, until the point of time t1 at which the said velocity value certainly will have been reached, the test sample P will be transported into the waste container 26. During this period of time (operating condition 7a in line g of FIG. 8), according to FIGS. 7a and 8, nozzle D1 is in operation, nozzle D2 is not in operation, cutting element M1 is open and cutting element M2 is closed. At the point of time t1 cutting element M1 makes a cut (FIG. 7b), nozzle D2 is activated and cutting element M2 is opened. Nozzle D1 will be switched off just shortly after t1 to guarantee that the test sample P which has been cut off at t1 will get into the waste container 26.

Subsequently the cutting element M1 remains closed, the nozzle D1 is not in operation and the nozzle D2 is in operation and transports the test sample P to the count tester 3. This corresponds to FIG. 7c and to the operating condition 7c in line g of FIG. 8.

At the point of time t2 (condition according to FIG. 7d), there follows a cut by the cutting element M2. The cut-off test sample P gets perfectly to the count tester 3 whereby the nozzle D2 will be switched off just shortly after t2. Subsequently, the condition according to FIG. 7a is present again and the test sample P is transported into the waste container 26 until the next determination of the count. The duration of the time period between t1 and t2 is defined by a given number N of pulses of the tachometer signal (FIG. 8, line b) the said number N corresponding to a given length Delta L of preferably 100 meters of the test sample P.

As the time period between the cuts of the cutting elements M1 and M2 (i.e. the time period between t1 and t2) is exactly definable by the tachometer signal, there results for the determination of count an exact lenght of the test sample and a standard lenght can easily be chosen.

I claim:

1. In apparatus for the automatic determination of the count of a textile test sample in the form of yarns, rovings or slivers, having a device for taking off definite lengths of a test sample from a supply, scales and an evaluation unit, the improvement which comprises means arranged in the path of the test sample upstream of the scales for forming the test sample taken off at any one time into a ball-like bundle and means for depositing the ball-like bundle on the scales for the making of a weight measurement.

2. Apparatus according to claim 1, including means for removing the bundle from the scales after said measurement.

3. Apparatus according to claim 2, wherein said means for forming the ball-like bundle includes a housing and a test sample transport line which ends in the side of said housing and is actuated by compressed air.

4. Apparatus according to claim 3, wherein said housing has a bell-shaped upper part and a plate-shaped lower part movable relative to the upper part.

5. Apparatus according to claim 4, wherein said transport line ends tangentially in said bell-shaped upper part of said housing.

6. Apparatus according to claim 4, wherein said plate-shaped base part is arranged above said scales and designed so that it can be lowered onto the scales.

7. Apparatus according to claim 2, wherein said means for removing the ball-like bundle from the scales includes a blow nozzle arranged to contact the ball-like bundle with a stream of air.

8. Apparatus according to claim 5, wherein said bell-shaped upper part takes the form of two joined frustum-shaped parts, the ratio of whose heights is approximately 2:1 and the ratio of whose angles of slope is approximately 1:1.4.

9. Apparatus according to claim 8, wherein said transport line for the test sample ends in said bell-shaped upper part at the zone where said two frustum-shaped parts are joined together.

10. Apparatus according to claim 9, wherein the axis of said transport line runs obliquely downwards in the region where it discharges into said upper part of said housing and is directed against the inner wall of said housing in the zone where the upper part and the base part of the housing meet.

11. The apparatus according to claim 1 in combination with an evenness testing device, wherein the apparatus of claim 1 is connected to the evenness testing device via a transport line, and there is provided an evaluation unit common to both said evenness testing device and the apparatus of claim 1.

12. The combination according to claim 11, wherein said evenness testing device has a feed device and a suction exhaust nozzle for the test sample, and wherein said transport line is connected to suction exhaust nozzle.

13. The combination according to claim 12, including a switch point to be used as desired to pass the test sample either to the transport line or to another line leading to a container.

14. The combination according to claim 13, wherein said suction exhaust nozzle is designed as a switch point and consists of two nozzles and a common intake joined to the said two nozzles.

15. The combination according to claim 14, including cutting means adjacent each of said two nozzles for cutting off the test sample.

16. The combination according to claim 15, wherein said cutting means are arranged between said common intake and said two nozzles.

17. The combination according to claim 15, wherein said cutting means are controllably actuable in response to signals from said feed device to obtain a defined length of the test sample for the determination of the count.

18. In a method for determining the weight per unit length of a textile strand, the steps of disposing a portion of the textile strand in an air stream moving toward a chamber; allowing a predetermined length of said strand suitable for weighing to move with said air stream; forming said predetermined length into a ball-like bundle in said chamber depositing said ball-like bundle made up of said predetermined length of textile strand on a weighing scale; and determining the weight per unit length of said textile strand from the weight of said predetermined length of said strand as measured by said scale.

* * * * *